US00PP31594P3

(12) United States Plant Patent
Schoone

(10) Patent No.: US PP31,594 P3
(45) Date of Patent: Mar. 24, 2020

(54) ***PHALAENOPSIS* PLANT NAMED 'FANCY FRECKLES'**

(50) Latin Name: *Phalaenopsis hybrida*
Varietal Denomination: Fancy Freckles

(71) Applicant: FLORICULTURA B.V., Heemskerk (NL)

(72) Inventor: Rene Schoone, Assendelft (NL)

(73) Assignee: Floracultura B.V., Heemskerk (NL)

( * ) Notice: Subject to any disclaimer, the term of this patent is extended or adjusted under 35 U.S.C. 154(b) by 0 days.

(21) Appl. No.: 16/350,080

(22) Filed: Sep. 21, 2018

(65) Prior Publication Data

US 2019/0098820 P1 Mar. 28, 2019

Related U.S. Application Data

(60) Provisional application No. 62/561,900, filed on Sep. 22, 2017.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

(56) References Cited

PUBLICATIONS https://www.orchids.org/grexes/phalaenopsis-fancy-freckles Orchid Hybrid *Phalaenopsis*—'Fancy Freckles' (retrieved from the Internet on Jun. 12, 2019( (2 pages total).*

* cited by examiner

*Primary Examiner* — Susan McCormick Ewoldt
(74) *Attorney, Agent, or Firm* — C. A. Whealy

(57) ABSTRACT

A new and distinct cultivar of *Phalaenopsis* plant named 'Fancy Freckles', characterized by its upright plant habit; moderately vigorous growth habit; relatively short dark green-colored leaves; strong flowering stems; freely flowering habit with typically about four racemes per plant, each inflorescence with numerous flowers; and light pale yellow-colored flowers with red purple-colored dots and spots and red purple-colored labellum.

2 Drawing Sheets

Botanical designation: *Phalaenopsis hybrida.*
Cultivar denomination: 'FANCY FRECKLES'.

BACKGROUND OF THE INVENTION

The present invention relates to a new and distinct cultivar of *Phalaenopsis* plant, botanically known as *Phalaenopsis hybrida,* known by the breeder's reference 280535 and hereinafter referred to by the name 'Fancy Freckles'.

The new *Phalaenopsis* plant is a product of a planned breeding program conducted by the Inventor in Heemskerk, The Netherlands. The objective of the breeding program is to develop new rapid growing and freely flowering *Phalaenopsis* plants with good leaf shape and unique and attractive flower patterns and coloration.

The new *Phalaenopsis* plant originated from a cross-pollination in 2005 in Heemskerk, The Netherlands of *Phalaenopsis hybrida* 'Diamond Beauty', not patented, as the female, or seed, parent with *Phalaenopsis hybrida* 'Snow Leopard', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in 2013.

Asexual reproduction of the new *Phalaenopsis* plant by in vitro meristem propagation in a controlled environment in Heemskerk, The Netherlands since July, 2013 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Fancy Freckles'. These characteristics in combination distinguish 'Fancy Freckles' as a new and distinct *Phalaenopsis* plant:

1. Upright plant habit.
2. Moderately vigorous growth habit.
3. Relatively short dark green-colored leaves.
4. Strong flowering stems.
5. Freely flowering habit with typically about four racemes per plant, each inflorescence with numerous flowers.
6. Light pale yellow-colored flowers with red purple-colored dots and spots and red purple-colored labellum.

Plants of the new *Phalaenopsis* can be compared to plants of the female parent, 'Diamond Beauty'. Plants of the new *Phalaenopsis* differ primarily from plants of 'Diamond Beauty' in the following characteristics:

1. Flowers of plants of the new *Phalaenopsis* have more dots and spots than flowers of plants of 'Diamond Beauty'.
2. Flowers of plants of the new *Phalaenopsis* have smaller dots and spots than flowers of plants of 'Diamond Beauty'.

Plants of the new *Phalaenopsis* can be compared to plants of the male parent, 'Snow Leopard'. Plants of the new *Phalaenopsis* differ primarily from plants of 'Snow Leopard' in flower color as flowers of plants of the new *Phalaenopsis* are light pale yellow in color whereas flowers of plants of 'Snow Leopard' are pink in color.

Plants of the new *Phalaenopsis* can be compared to plants of *Phalaenopsis hybrida* 'Yellow Umbrella', not patented. In side-by-side comparisons, plants of the new *Phalaenopsis* differ primarily from plants of 'Yellow Umbrella' in flower color as flowers of the new *Phalaenopsis* have more dots and spots than flowers of plants of 'Yellow Umbrella'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'Fancy Freckles' grown in a container.

The photograph at the top of second sheet is a close-up view of a typical flower of 'Fancy Freckles'.

DETAILED BOTANICAL DESCRIPTION

The aforementioned photographs and following observations and measurements describe plants grown during the late summer in 10-cm containers in a glass-covered greenhouse in Heemskerk, The Netherlands and under cultural practices typically used in commercial *Phalaenopsis* production. During the production of the plants, day temperatures ranged from 20° C. to 22° C. and night temperatures averaged 18° C. and light levels ranged from 5 klux to 10 klux. Plants were three years old when the photographs were taken and two years eight months old when the description was taken. In the following description, color references are made to The Royal Horticultural Society Colour Chart, 2015 Edition, except where general terms of ordinary dictionary significance are used.

Botanical classification: *Phalaenopsis hybrida* 'Fancy Freckles'.

Parentage:

*Female parent.*—*Phalaenopsis hybrida* 'Diamond Beauty', not patented.

*Male parent.*—*Phalaenopsis hybrida* 'Snow Leopard', not patented.

Propagation:

*Type.*—By in vitro meristem propagation.

*Time to initiate roots, summer.*—About two weeks at temperatures about 28° C. to 30° C.

*Time to initiate roots, winter.*—About three weeks at temperatures about 28° C. to 25° C.

*Time to produce a rooted young plant, summer and winter.*—About 20 to 25 weeks at temperatures about 28° C. to 30° C.

*Root description.*—Fine, fibrous; typically light yellowish white in color, actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically about four racemes per plant, each inflorescence with numerous flowers; monopodial; moderately vigorous growth habit and moderate growth rate.

*Plant height, substrate level to top of foliar plane.*—About 8 cm.

*Plant height, substrate level to top of inflorescences.*—About 38.2 cm.

*Plant diameter or spread.*—About 22.5 cm.

Leaf description:

*Arrangement and quantity.*—Distichous, simple; sessile; about six per plant.

*Length.*—About 18.1 cm.

*Width.*—About 6.4 cm.

*Aspect.*—Horizontal to upright to slightly arching.

*Shape.*—Narrowly elliptic to oblanceolate; slightly carinate.

*Apex.*—Acute, unequal.

*Base.*—Sheathing.

*Margin.*—Entire; slightly revolute.

*Texture and luster, upper surface.*—Smooth, glabrous; slightly glossy.

*Texture and luster, lower surface.*—Smooth, glabrous; moderately glossy.

*Venation pattern.*—Camptodromous.

*Color.*—Developing leaves, upper surface: Close to between NN137B and 147A. Developing leaves, lower surface: Close to 146B, towards the margins, slightly tinged with close to 146A. Fully expanded leaves, upper surface: Close to NN137A to NN137B; venation, close to NN137A. Fully expanded leaves, lower surface: Close to 146B; towards the margins, slightly tinged with close to 146A; venation, close to 144A.

Inflorescence description:

*Appearance and flowering habit.*—Showy zygomorphic flowers arranged on axillary simple or branched racemes; typically about four racemes per plant; each inflorescence with about seven open flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about two months after flower bud initiation.

*Flower longevity.*—Long flowering period, individual flowers maintain good substance for about four to six months on the plant; flowers not persistent.

*Inflorescence length* (*lowermost flower to inflorescence apex*).—About 10.4 cm.

*Inflorescence width.*—About 10.8 cm.

*Flower buds.*—Height: About 1.8 cm. Diameter: About 1.4 cm. Shape: Broadly oblong. Color: Close to between 145B and 150B; distally, close to N144D.

*Flower diameter.*—About 5.8 cm by 6.4 cm.

*Flower depth.*—About 2.9 cm.

*Petals, quantity and arrangement.*—Three, two lateral petals and one center petal transformed into a labellum.

*Lateral petals.*—Length: About 3 cm. Width: About 3.4 cm. Shape: Roughly rhomboidal. Apex: Rounded. Margin: Entire. Texture and luster, upper surface: Smooth, glabrous, velvety; matte. Texture and luster, lower surface: Smooth, glabrous, slightly velvety; matte. Color: When opening, upper surface: Close to between 150C and 154D; fine dots and spots, close to 59A. When opening, lower surface: Close to between 150C and 154D; fine dots and spots, close to 182C. Fully opened, upper surface: Close to 1C; fading towards the base to close to NN155A; at the attachment point with the column, close to N78C; fine dots and spots, close to 59B; color does not fade with development. Fully opened, lower surface: Close to 1C; fading towards the base to close to NN155A; fine dots and spots, close to 182C; color does not fade with development.

*Labellum.*—Appearance: Tri-lobed with two lateral lobes and a central lobe. Length, lateral lobe: About 1.5 cm. Width, lateral lobes: About 9 mm. Length, central lobe: About 2.9 cm. Width, central lobe: About 1.5 cm. Shape, lateral lobes: Obovate. Shape, central lobe: Ovate to roughly rhomboidal. Apex, lateral lobes: Obtuse. Apex, central lobe: Cleft with two moderately long recurved cirrose tips, about 6 mm in length and about 1.1 cm in width. Margins, lateral lobes: Entire. Margins, central lobe: Entire. Texture and luster, upper and lower surfaces: Smooth, glabrous, velvety; matte. Callosities: Located at the base of the labellum and attachment point of the lateral petals; about 3.5 mm in length, about 4 mm in width and about 3.5 mm in height. Color: When opening, upper surface: Lateral lobes: Close to 4D; fading towards the base to close to 7D; apex and margins, close to or lighter than between 53D and 59C; stripes, close to 59B. Central lobe: Close to 163C to 163D tinged with close to 184A; fading towards the margins to close to 184A; fading towards the apex, close to 59D; fine dots, close to 59A; cirrose apices, close to N155D. Callosities: Close to 12A; fine dots, close to 59A. When opening, lower surface: Lateral lobes: Close to 160B; towards the margins, close to 59B and 59C. Central lobe: Close to 179D; fading towards the base to close to 11A to 11D; fading towards the margins and apex to close to 59C to 59D and 64B to 64C; cirrose apices, close to N155D. Fully opened, upper surface: Lateral lobes: Close to 4D; fading towards the base to close to or lighter than 7D; apex and margins, close to or lighter than between 53D and 59C; stripes, close to 59B. Central lobe: Close to 163C to 163D tinged with close to 184A; fading towards the margins to close to 184A; fading towards the apex, close to 59D; fine dots, close to 59A; cirrose apices, close to N155D. Callosities: Close to 12A; fine dots, close to 59A. Fully opened, lower surface: Lateral lobes: Close to 160C; towards the margins, close to 59B and 59C. Central lobe: Close to 179D; fading towards the base to close to 11A to 11D; fading towards the margins and apex to close to 59C to 59D and 64C; cirrose apices, close to N155D.

*Sepals.*—Quantity and arrangement: Three, two lower lateral sepals and one upper dorsal sepal. Length, lateral sepal: About 3.2 cm. Width, lateral sepals: About 2.1 cm. Length, dorsal sepal: About 3.2 cm. Width, dorsal sepal: About 2.3 cm. Shape, lateral and dorsal sepals: Elliptic. Apex, lateral sepal: Broadly and bluntly acute. Apex, dorsal sepals: Obtuse. Base, lateral and dorsal sepals: Truncate. Margin, lateral and dorsal sepals: Entire. Texture and luster, lateral and dorsal sepals, upper and lower surfaces: Smooth, glabrous, velvety; matte. Color: When opening, upper surface: Lateral sepals: Close to 150C and 154D; fine dots, close to 59A. Dorsal sepals: Close to between 150B, 150C and 154D; fine dots, close to 59A. When opening, lower surface: Lateral sepals: Close to N144D; fading towards the base to close to 145C; fine dots, close to 197B. Dorsal sepals: Close to N144D; fine dots, close to 197B. Fully opened, upper surface: Lateral and dorsal sepals: Close to 1C; fading towards the base to close to NN155A; at the attachment point with the column, tinged with close to N78C; fine dots, close to 59B; color does not fade with development. Fully opened, lower surface: Lateral and dorsal sepals: Close to 151C; fading towards the margins and base to close to 150C; fine dots, close to 197B; color does not fade with development.

*Peduncles.*—Length: About 36.6 cm. Diameter: About 5 mm. Strength: Very strong. Aspect: Upright to about 25° from vertical. Texture and luster: Smooth, glabrous; matte. Color: Close to 147A with fine dots, close to 144A to 144B.

*Pedicels.*—Length: About 3.4 cm. Diameter: About 3 mm. Strength: Moderately strong. Aspect: About 30° from peduncle axis. Texture and luster: Smooth, glabrous; matte. Color: Close to N144C; distally, fading to close to 150D.

*Reproductive organs.*—Androecium: Column length: About 1 cm. Column width: About 5.5 mm. Column color: Close to 155C. Pollinia quantity: Two. Pollinia diameter (per two pollinia): About 3 mm. Pollinia color: Close to 17B. Gynoecium: Stigma length: About 4 mm. Stigma width: About 4 mm. Stigma shape: Reniform. Stigma color: Close to NN155B. Ovary length: About 1.6 cm. Ovary diameter: About 1 mm. Ovary color: Close to 144D. Seeds and fruits:To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 10° C. to about 40° C. and to be suitable for USDA Hardiness Zone 10.

It is claimed:

1. A new and distinct *Phalaenopsis* plant named 'Fancy Freckles' as illustrated and described.

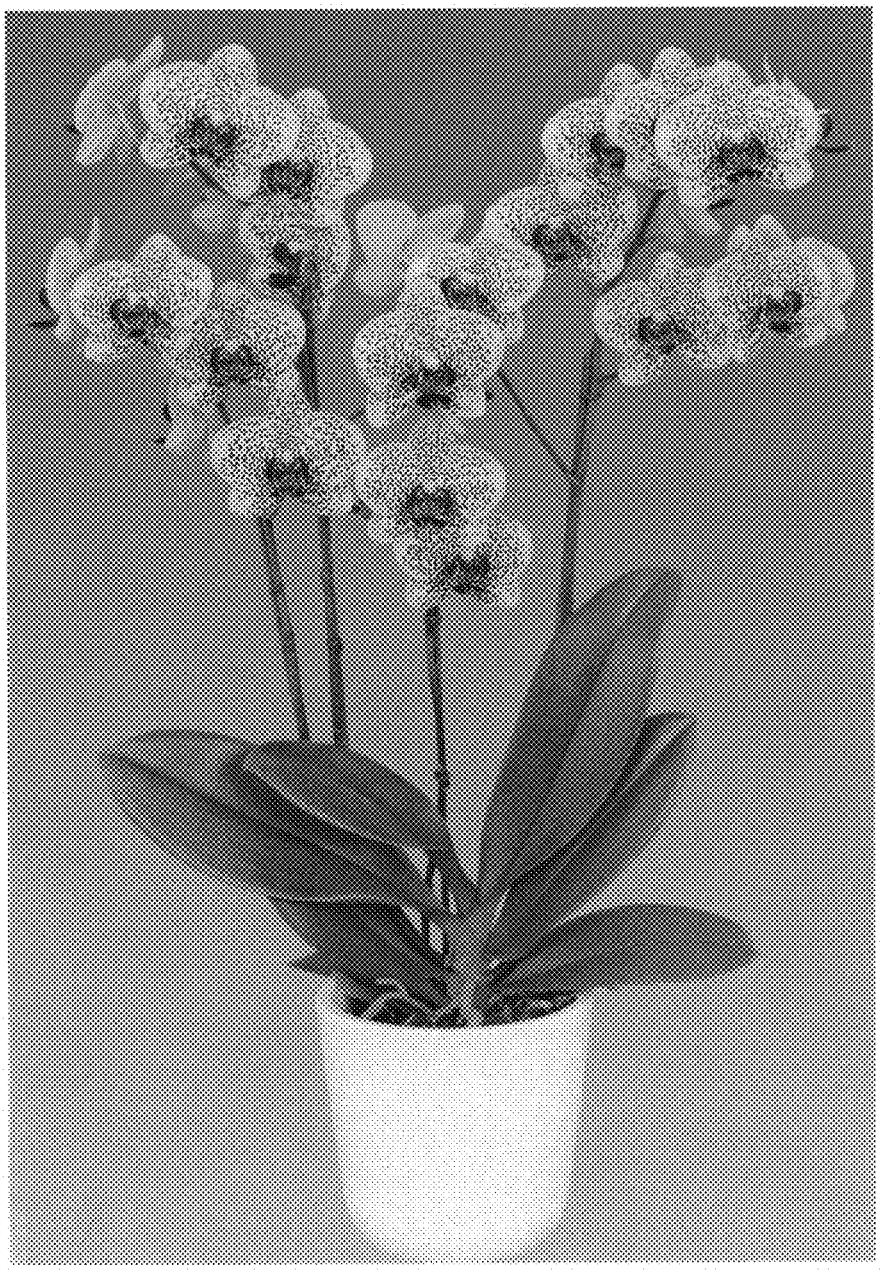

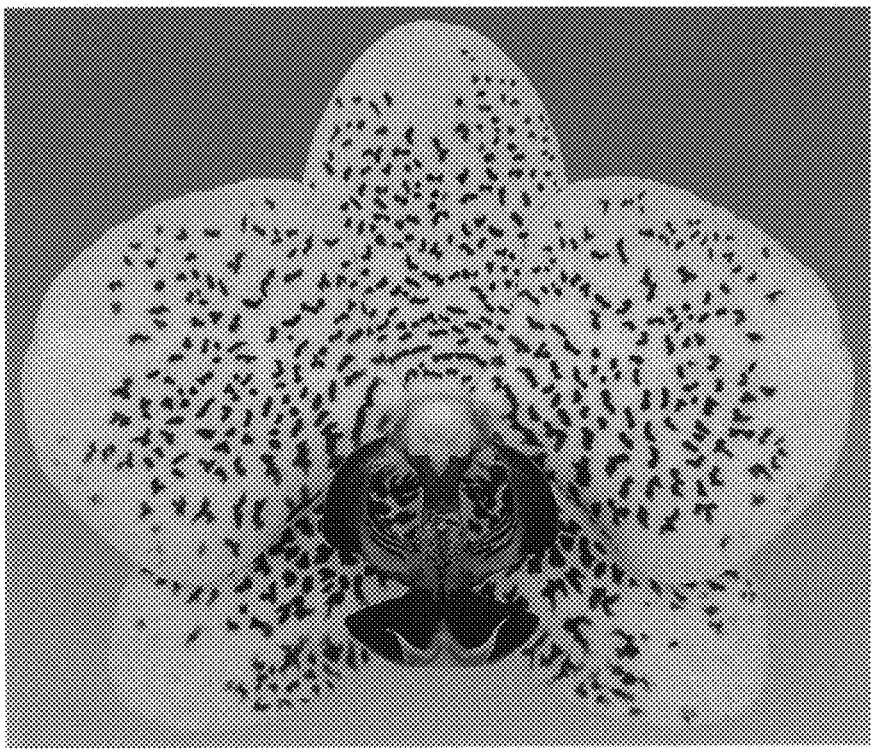

* * * * *